United States Patent
Meirandres

(10) Patent No.: US 10,466,130 B2
(45) Date of Patent: Nov. 5, 2019

(54) TEST DEVICE, A TEST SYSTEM AND A METHOD FOR TESTING A MECHANICAL PRESSURE SENSOR

(71) Applicant: Multitest elektronische Systeme GmbH, Rosenheim (DE)

(72) Inventor: Markus Meirandres, Rosenheim (DE)

(73) Assignee: Multitest Elektronische Systeme GmbH, Rosenheim (DE)

(*) Notice: Subject to any disclaimer, the term of this patent is extended or adjusted under 35 U.S.C. 154(b) by 347 days.

(21) Appl. No.: 15/443,190

(22) Filed: Feb. 27, 2017

(65) Prior Publication Data

US 2018/0246002 A1    Aug. 30, 2018

(51) Int. Cl.
*G01L 27/00* (2006.01)
*G01N 3/10* (2006.01)

(52) U.S. Cl.
CPC .............. *G01L 27/00* (2013.01); *G01N 3/10* (2013.01)

(58) Field of Classification Search
CPC ......... G01L 27/00; G01L 27/005; G01N 3/10; G01N 3/12
USPC ...................................... 73/1.57, 1.68, 865.9
See application file for complete search history.

(56) References Cited

U.S. PATENT DOCUMENTS

| | | | | |
|---|---|---|---|---|
| 3,597,981 A | * | 8/1971 | Wakabayashi | B41J 29/393 73/865.9 |
| 5,900,530 A | * | 5/1999 | O'Brien | G01L 27/005 73/1.57 |
| 2011/0122419 A1 | * | 5/2011 | Orthner | G01N 3/20 356/601 |
| 2016/0118210 A1 | * | 4/2016 | Beroz | H01H 35/26 200/81 R |

* cited by examiner

*Primary Examiner* — Benjamin R Schmitt
(74) *Attorney, Agent, or Firm* — Lewis Roca Rothgerber Christie LLP

(57) ABSTRACT

A test device (400) for testing a mechanical pressure sensor (610) is described. The Device (400) comprises a mechanical pressure dummy (621), and an air chamber (320) having an elastic side section (222), wherein an increasing of air pressure in the air chamber (320) causes the elastic side section (222) to bulge and to press the mechanical pressure dummy (621) in a test position (D').

17 Claims, 6 Drawing Sheets

TEST DEVICE, A TEST SYSTEM AND A METHOD FOR TESTING A MECHANICAL PRESSURE SENSOR

FIELD OF INVENTION

An embodiment of the invention relates to a test device for testing a mechanical pressure sensor. Further, an embodiment relates to a test system for a parallel test of a plurality of mechanical pressure sensors. Moreover, an embodiment relates to a method of testing a mechanical pressure sensor.

BACKGROUND OF THE INVENTION

Mechanical pressure sensors are used in many electrical devices. Fingerprint sensors are examples for mechanical pressure sensors and are used in smart-phones and the like. In the back end process the mechanical pressure sensors are tested to prove their functionality. The so called ATE (automated test equipment) tests a plurality of electrical components to subsequently sort the tested electrical components.

SUMMARY OF THE INVENTION

There may be a need to provide a test device, a test system, and a method of testing a mechanical pressure sensor. In particular, there may be a need to test many mechanical pressure sensors parallel and accurately. In order to meet the need defined above a test device, a test system and a method of testing mechanical pressure sensors are provided according to the independent claims.

According to an embodiment of the invention a test device for testing a mechanical pressure sensor comprises:
a mechanical pressure dummy, and
an air chamber having an elastic side section. The air chamber is configured such that an increasing of air pressure in the air chamber causes the elastic side section to bulge and to press the mechanical pressure dummy in a test position.

According to a further embodiment of the invention a test system for parallel testing of a plurality of mechanical pressure sensors comprises:
a plurality of mechanical pressure dummies, and
a plurality of air chambers each having an elastic side section. The plurality of the elastic side sections are arranged so that increasing of air pressure in the plurality of air chambers causes each of the elastic side sections to bulge and to press each of the plurality of mechanical pressure dummies in a test position.

According to a further embodiment of the invention, a method of testing a mechanical pressure sensor is described. The method comprises:
providing a mechanical pressure dummy,
providing an air chamber having an elastic side section, and
increasing of air pressure in the air-tight cavity so that the elastic side section bulges and causes the mechanical pressure dummy to be pressed in a test position.

The expression "test device" may describe a piece of equipment or a mechanism designed to serve the purpose of performing a check or characterization of an electronic component, e.g. a mechanical pressure sensor, such as a fingerprint sensor. The expression "test system" may describe an apparatus comprising a plurality of similar test devices. The expression "mechanical pressure sensor" may describe a device that responds to a mechanical pressure stimulus and transmits a resulting electrical signal. In particular, the mechanical pressure sensor may be a fingerprint sensor which responds to a pressure stimulus of a fingertip or the like by transmitting a resulting electrical signal.

The expression "mechanical pressure dummy" may describe an imitation of a surface having a certain mechanical surface hardness so that the mechanical pressure dummy is suitable for simulating a mechanical surface of a regularly sensed specimen. In particular, the mechanical pressure dummy may be a fingerprint dummy. Hence, the expression "mechanical pressure dummy" may describe an imitation or copy of a fingertip on a surface. In particular, the fingerprint dummy and/or the mechanical pressure dummy may be made from silicone.

The expression "air chamber" may describe something for forming an enclosed space or cavity which shape may vary widely. In particular, the air chamber may enclose a fluid or gas (as air) of varying pressure. The air chamber may comprise at least an inlet and/or outlet for applying the different pressure conditions. The air chamber may be air-tight so that the air pressure may remain sufficiently constant in the air chamber. In particular, the expression "air pressure" may describe any pressure condition of any fluid in the air chamber. Hence, the expression "air" may chemically include any gas or fluid or any mixture of these. The air chamber may comprise an air chamber cavity and an elastic side section covering an opening of the air chamber cavity. The expression "elastic side section" may describe a part of the air chamber capable of being stretched or expanded when changing the air pressure in the air chamber and resuming former shape. The elastic sides section may comprise an elastic membrane. In particular, the elastic side section may be a part of an elastic membrane.

The term "to bulge" may describe that something extends outward beyond the usual. In particular, the elastic side section may bulge followed by a raised air pressure in the air chamber.

The expression "test position" may describe the position where the mechanical pressure sensor, or the fingerprint dummy makes a mechanical contact to the mechanical pressure sensor, or to the fingerprint sensor, respectively. The pressing of the mechanical pressure, or of the fingerprint dummy, respectively, may go outward in the same direction like the bulging of the elastic side section. The force by which the mechanical pressure dummy, or fingerprint dummy, is pressed against the mechanical pressure sensor, or fingerprint sensor, may be similar to the pressure exerted by a real mechanical specimen, or fingertip, respectively. There may be a contact block or a socket exerting a counterforce on the mechanical pressure sensor (or fingerprint sensor), so that the mechanical pressure sensor (or fingerprint sensor) does not lift off (an aligned position) by the pressure force being exerted by the mechanical pressure dummy (or fingerprint dummy). Further, there may be a socket having contacts which are adapted to contact to contact terminals of the mechanical pressure sensor (or fingerprint sensor) when the contact block exerts the counterforce on the mechanical pressure sensor (or fingerprint sensor). Moreover, the contact force being exerted by the contacts of the socket may be smaller than the pressure force by which the mechanical pressure dummy (or fingerprint dummy) is pressed into the test position. In particular, the carrier may be held or brought into in the aligned position by vacuum cups when the mechanical pressure sensor (or fingerprint sensor) is not contacted.

A basic idea may be that having an air-tight chamber with an elastic side section may allow for moving a mechanical pressure dummy (fingerprint dummy) in a test position where the mechanical pressure dummy (fingerprint dummy) is mechanically contacting the mechanical pressure sensor (fingerprint sensor) to be tested. This may be achieved by raising the air pressure in the air chamber so that the elastic side section bulges. The mechanical pressure dummy (fingerprint dummy) may be directly moved by the bulging of the elastic side section. However, bulging of the elastic side section may also indirectly cause the mechanical pressure dummy (fingerprint dummy) to move, if there are any mechanically transmissions coupled between the elastic side section and the mechanical pressure dummy (fingerprint dummy). From the perspective of the test device the mechanical pressure dummy (fingerprint dummy) may be lifted since the elastic sides section bulges. However, the orientation of the test device itself may have the effect that the mechanical pressure dummy (fingerprint dummy) is moved in any possible direction when seen from outside of the test device. Hence, the mechanical pressure dummy (fingerprint dummy) may be lifted, moved sideward, or lowered by considering of having the test device different operational directions which are usual for ATE (automated test equipment).

The air pressure in the air chamber may be proportional to the contact pressure which presses the mechanical pressure dummy (fingerprint dummy) in the test position. In particular, the test position of the mechanical pressure dummy (fingerprint dummy) may be the position where the mechanical pressure dummy (fingerprint dummy) mechanically contacts the fingerprint sensor.

The air pressure in the air chamber may be adjustable so that the mechanical contact pressure by which the mechanical pressure dummy (fingerprint dummy) is pressed into the test position and against the mechanical pressure sensor (fingerprint sensor) is adjustable depending on the air pressure in the air chamber.

According to an exemplary embodiment of the test device, the bulging of the elastic side section goes in the same direction like a movement of the mechanical pressure dummy.

It may be appropriate to directly transmit the movement of the bulging elastic side section into a movement of the mechanical pressure dummy (fingerprint dummy). This may allow for an accurate mechanical contact pressure of the mechanical pressure dummy (fingerprint dummy). The test position may be an elevated, lifted or raised position since the bulging of the elastic side section may be outward.

According to an exemplary embodiment of test device, the air chamber comprises an air chamber cavity having an elevated edge so that pressing the elastic side section against the elevated edge makes an air-tight seal.

The expression "elevated edge" may describe a raised rim. The elevated edge may be a boundary of the air chamber cavity on which the elastic sided section or the elastic membrane may be pressed to.

The expression "air-tight sealing" may be described by making the air chamber secure against leakage. In particular, the elastic side section being pressed on the elevated edge may form the air-tight sealing.

The expression "air chamber cavity" may describe a cup shaped hollow part of the air chamber. The air chamber cavity may comprise an opening which is covered by the elastic side section or membrane. In particular, the air chamber cavity may comprise the elevated edge. By assembling the test device, the elastic side section may be automatically pressed towards the air chamber cavity, so that the air chamber is air-tight. In particular, the air chamber may be air-tight when the mechanical pressure dummy (fingerprint dummy) is in the test position and when the mechanical pressure dummy (fingerprint dummy) is in an initial or rest position.

According to an exemplary embodiment the test device, further comprises a piston, wherein the mechanical pressure dummy is arranged at one piston end, and wherein the elastic side section is arranged at an opposite piston end.

The term "piston" may describe a sliding piece which may consist of a short cylindrical body fitting within a cylindrical vessel along which it moves back and forth. The movement of the piston may be directly or indirectly forced by the bulging and the resuming of the former shape of the elastic side section. In particular, the fingerprint dummy is arranged at one piston end wherein the elastic side section is arranged at an opposite piston end. The piston may be exchangeable so that the mechanical pressure dummy may be adapted according to the purpose of testing a specific mechanical pressure sensor. The piston is designed to accept inserts that may represent a certain mechanical behavior, e.g. a finger or a surface with a specific pattern. In particular, the piston may be arranged between the elastic side section and the mechanical pressure sensor to be tested.

The expression "one piston end" may describe a first one of two sides of the piston which sides are lying opposite in the movement direction of the piston. The one piston end may directly or indirectly contact or couple to the mechanical pressure dummy (fingerprint dummy). The opposite piston end may directly or indirectly contact or couple to the elastic side section. The mechanical pressure dummy (fingerprint dummy) may be attached to the piston or may be an integral part of the piston. In particular, the elastic side section or elastic membrane may be arranged between the opposite piston end (opposite to the end of the mechanical pressure dummy, or fingerprint dummy end, respectively) and the air chamber cavity.

According to an exemplary embodiment of the test device, the piston is guideable by a piston guide so that the mechanical pressure dummy is moveable perpendicularly into the test position.

In particular, the fingerprint dummy is moved perpendicularly into the test position.

The expression "piston guide" may describe the hollow cylindrical vessel for directing the motion of the piston. A perpendicular movement of the mechanical pressure dummy (fingerprint dummy) into the test position and towards the mechanical pressure dummy (fingerprint sensor) may be appropriate for making a defined and flat mechanical contact with the mechanical pressure dummy (fingerprint sensor).

According to an exemplary embodiment the test device further comprises a return spring, wherein the return spring is clamped between the piston and the piston guide so that the piston is held in an initial position when there is ambient air pressure in the air chamber.

The expression "return spring" may describe a resilient or elastic piece to restore the piston to a former or to a normal state when the air pressure is not increased.

The expression "clamped" may describe the return spring bracing between two support surfaces between which the return spring is compressed.

The expression "initial position" may describe a rest position, that is, the former or normal state of the piston. In particular, the return spring forces the piston into the initial position or rest position before starting the testing when the air pressure is not increased and the mechanical pressure dummy (fingerprint dummy) is not pressed against the mechanical pressure sensor (fingerprint sensor).

The air chamber cavity may comprise the piston guide.

According to an exemplary embodiment a test system for parallel testing a plurality of mechanical pressure sensors comprises:

a plurality of test devices, wherein the air chambers are coupled by air ducts so that there is a pressure balance between the air chambers.

In particular, a plurality of fingerprint sensors comprises: a plurality of test devices, wherein the air chambers are coupled by air ducts so that there is a pressure balance between the air chambers.

The expression "air duct" may describe a channel by which the fluid or gas is piped between the air chambers. In particular, the air ducts may be regarded as inlets and/outlets by which the air chambers exchange the fluid or gas. The expression "pressure balance" may describe that after applying a defined air pressure by an air pressure supply from outside the air chambers reach a stable state in which each of the air chambers comprises the same air pressure in each air chamber.

In particular, when having a plurality of air chambers with elastic side sections, the elastic side sections may comprise the elastic membrane. Further, the elastic membrane may extend over the whole area of the air chamber cavities like a cover which continuously covers a group of air chamber cavities. The air chambers may be arranged in rows. Further, the rows of air chambers may be arranged side by side so that the air chambers may form an array.

There may be a plurality of air chamber cavities covered each by an elastic sides section, and a plurality of air chambers, wherein for each of them one air chamber has one side section and one respective mechanical pressure dummy (fingerprint dummy). Further, one mechanical pressure dummy (fingerprint dummy) may be pressed against a respective one of the mechanical pressure sensors (fingerprint sensors).

According to an exemplary embodiment of the test system, the bulging of the elastic side sections goes in the same direction like the movement of the mechanical pressure dummies.

In particular, the bulging of the elastic side sections goes in the same direction like the movement of the fingerprint dummies.

According to an exemplary embodiment of the test system, each of the air chambers comprise air chamber cavities having elevated edges so that pressing the elastic side sections against the elevated edges makes air-tight seals.

The air chambers may be grouped, e.g., into rows and the elevated edges may surround the group of air chambers. Several groups or rows of air chambers may be arranged side by side and form an array. The array of air chambers may be covered by one elastic membrane so that the elastic membrane is pressed against the elevated edges and forms an air-tight seal for each of the rows of air chambers. The air chambers may be integral parts of an air chamber plate.

According to an exemplary embodiment the test system further comprises a plurality of air ducts, wherein the air chambers are coupled by the air ducts so that there is a pressure balance between the air chambers.

According to an exemplary embodiment the test system, further comprises a plurality of pistons, wherein the mechanical pressure dummies are arranged at one piston ends, and wherein the elastic side sections are arranged at opposite piston ends.

In particular, the fingerprint dummies are arranged at one piston ends, and wherein the elastic side sections are arranged at opposite piston ends.

In particular, the elastic membrane comprising each side section may be arranged at the opposite side piston ends so that the elastic membrane may be arranged between the pistons and the air chamber cavities. By applying a higher air pressure in the air chambers, the elastic sides sections may mutually bulge and the elastic side sections may mutually move the pistons and the mechanical pressure dummies (fingerprint dummies) into the test position where the mechanical pressure dummies (fingerprint dummies) make mechanical contact to the fingerprint sensors. Each of elastic side section which may be a part of the elastic membrane may transmit the pressure homogeneously so that the forces being exerted on the pistons may be equal for each of the piston.

According to an exemplary embodiment of the test system, the pistons are guided by piston guides so that the mechanical pressure dummies are moved mutually and perpendicularly towards the mechanical pressure sensors. In particular, the pistons are guided by piston guides so that the fingerprint dummies are moved mutually and perpendicularly towards the mechanical pressure sensors.

According to an exemplary embodiment of the test system, comprises a plurality of return springs, wherein the return springs are clamped between the pistons and the piston guides so that the pistons are held in initial positions when there is ambient air pressure in the air chambers.

According to an exemplary embodiment of the method, the bulging of the elastic side section goes in the same direction like a movement of the mechanical pressure dummy.

In particular, the bulging of the elastic side section goes in the same direction like a movement of the fingerprint dummy.

According to an exemplary embodiment of the method, an air chamber cavity of the air chamber has an elevated edge, wherein the elastic side sections are pressed against the elevated edges of the air chamber cavity of the air chamber to make air-tight seals.

According to an exemplary embodiment of the method the mechanical pressure dummy is arranged at one piston end of the piston, and wherein the elastic side section being arranged at an opposite piston end of the piston.

In particular, the method further comprises a piston, wherein the fingerprint dummy is arranged at one piston end, and wherein the elastic side section being arranged at an opposite piston end.

According to an exemplary embodiment of the method, the piston is guided by a piston guide so that the mechanical pressure sensor (fingerprint dummy) is moved perpendicularly in the test position.

According to an exemplary embodiment of the method, further provides a return spring, wherein the return spring is clamped between the piston and the piston guide so that the piston is held in an initial position when there is ambient air pressure in the air chamber. The air chamber cavity may comprise the piston guide.

According to an exemplary embodiment of the method a plurality of air chambers are coupled by air ducts so that there is a pressure balance between the air chambers.

A carrier may have an array of mechanical pressure sensors (fingerprint sensors) interacting with the array of mechanical pressure sensors (fingerprint dummies) when the array of pistons are forced into the test position by mutually increasing the air pressure in the array of air chambers.

The explanations may apply equally to the test device, the test system and the method of testing a mechanical pressure sensor, or fingerprint sensor, respectively.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

DETAILED DESCRIPTION OF THE DRAWINGS

Figure 1:
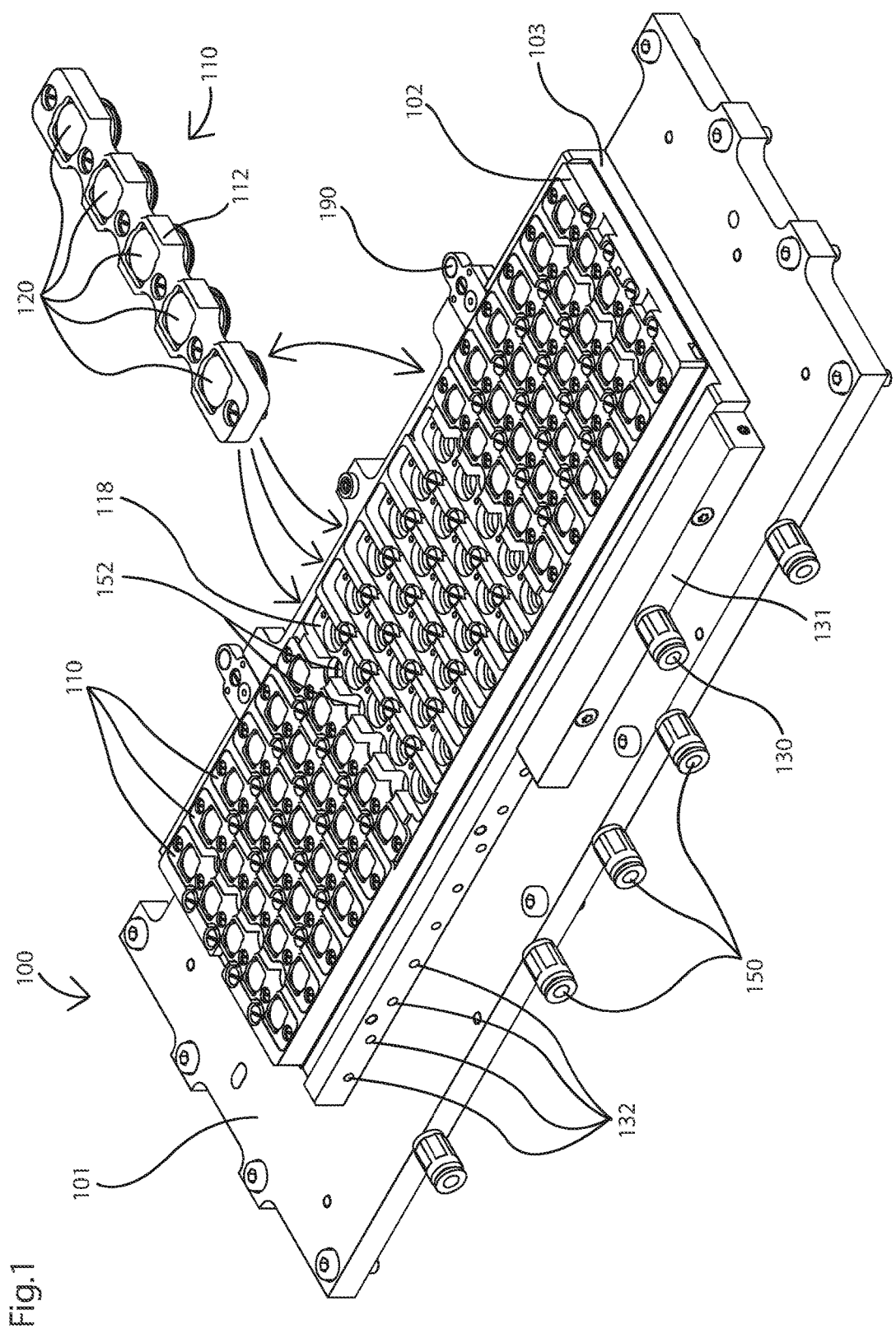
FIG. 1 shows a test system for testing a plurality of fingerprint sensors in a perspective view

The illustration in the drawings is schematically. In different drawings, similar or identical elements are provided with the same reference signs.

FIG. 1 shows a test system 100 for testing a plurality of fingerprint sensors (see 610 in FIG. 6 and FIG. 7) in a perspective view. The test system 100 comprises a base plate 101, an air pressure distribution plate 103, and a piston unit support plate 102. The air pressure distribution plate 103 is arranged between the base plate 101 and the piston unit support plate 102. The piston unit support plate 102 comprises a plurality of insertion openings 118 in each of which a piston unit 110 is inserted. Each piston unit 110 may comprise a piston support 112 adapted to receive a plurality of pistons 120. The pistons 120 may be arranged in a row of five pistons 120. Eighteen rows of pistons 120 may be arranged side by side forming an array of 5×18 pistons 120 on the piston unit support plate 102. Two air distribution manifolds 131 may be fixed to the air pressure distribution plate 103 (compare also FIG. 3). Each of the air distribution manifolds 131 may comprise an air pressure terminal 130 supplying a specific air pressure. The specific air pressure may be distributed to a plurality of air distribution holes 132 by each of the air distribution manifolds 131. Each one of the air distribution holes 132 drilled into the air distribution plate 103 may distribute the specific air pressure to one respective piston unit 110 which equals a row of five pistons 120 being arranged in one piston support 112. The number (eighteen) of piston units 110, the number of insertion openings 118, and the number of air distribution bores 132 may be equal. An air pressure distribution may be configured to supply equal air pressure to each of the pistons 120. The air pressure distribution may be explained in more detail in FIGS. 3 and 4.

Figure 2:
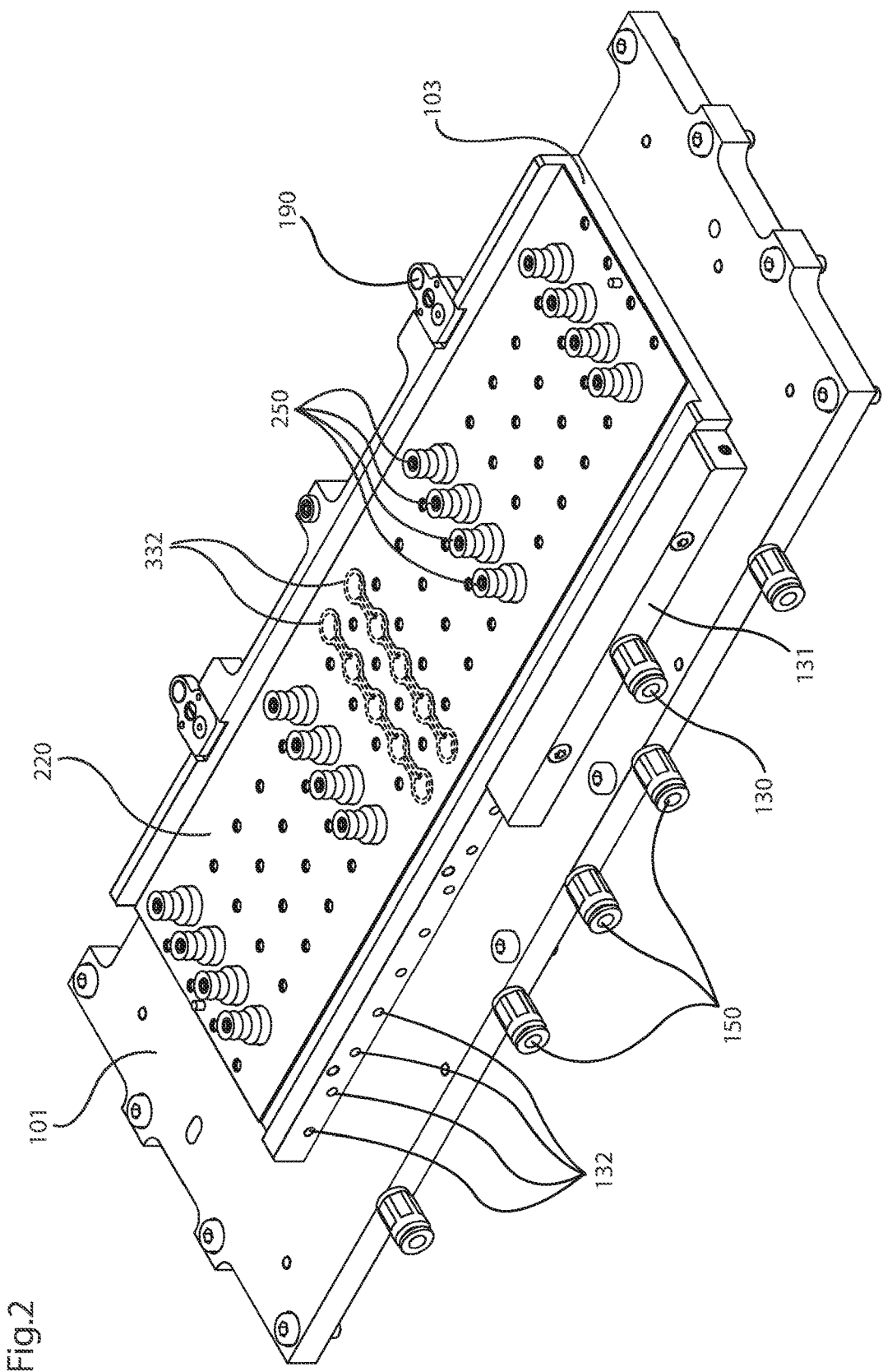
FIG. 2 shows a detail of the test system in a perspective view
Figure 5:
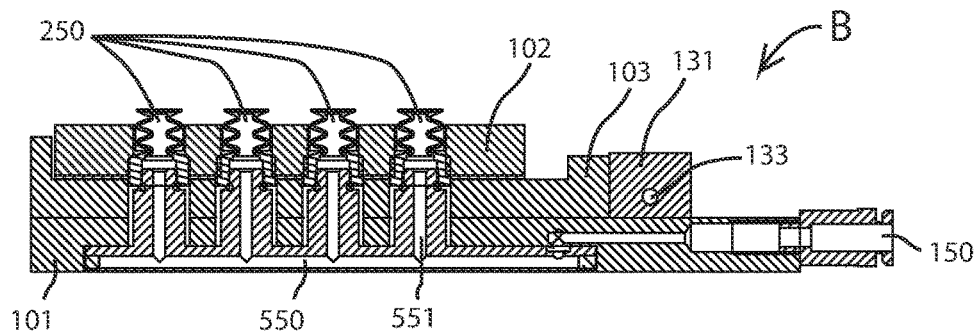
FIG. 5 shows a cross-sectional view through a vacuum supply of the test system

The base plate 101 may also comprise a plurality of vacuum fittings 150 which supply vacuum to a plurality of openings 152 in each of which a vacuum cup 250 is arranged (compare also FIG. 2 and FIG. 5). The plurality of vacuum cups 250 allow for sucking and fixing a carrier 600 (see FIG. 5 to FIG. 7) on the test system 100. The test system 100 may further comprise fiducial elements 190 for centring and aligning the carrier 600 relative to contact portions of contact sockets (not shown).

FIG. 2 shows a detail of the test system 100 in a perspective view when the piston unit support plate 102 along with the inserted piston units 110 have been removed. As a consequence, a membrane 220 is be visible which is arranged between the piston unit support plate 102 and the air pressure distribution plate 103. The membrane 220 may cover the complete area of the air pressure distribution plate 103 and comprises openings for the vacuum cups 250 and openings for screws by which the piston unit support plate 102 is fixed to the air pressure distribution plate 103. A silhouette of an elevated edge 332 indicates that beneath the membrane 200 the air pressure distribution plate 103 is structured comprising these elevated edges 332 (shown in FIG. 3).

Figure 3:
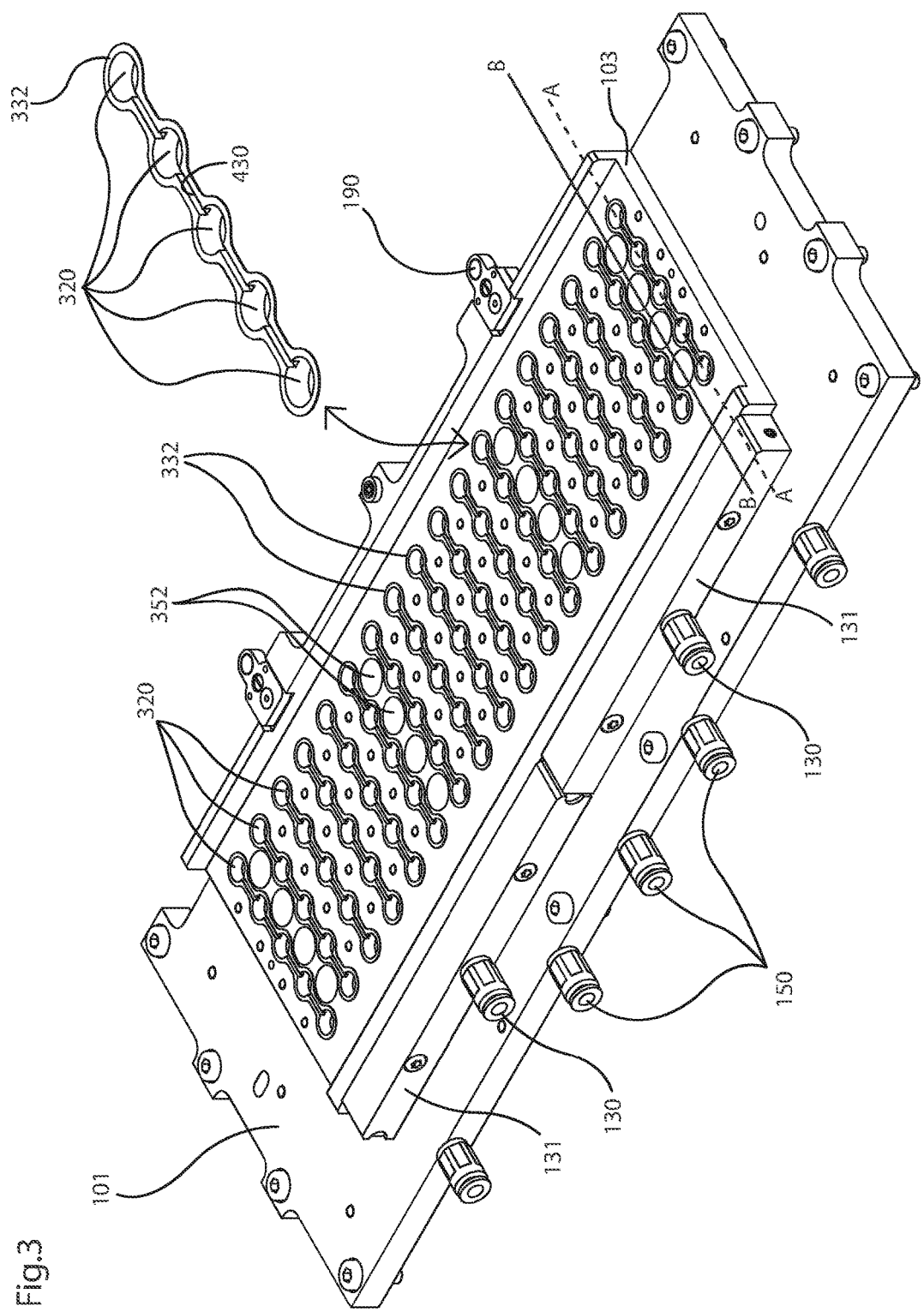
FIG. 3 shows a further detail of the test system in a perspective view

FIG. 3 shows a further detail of the test system 100 in a perspective view when the membrane 220 has been removed so that the structure of the air pressure distribution plate 103 becomes visible. The air pressure distribution plate 103 comprises a plurality of air chambers 320 which are arranged in eighteen rows of five air chambers 320 corresponding to the number of eighteen rows of five pistons 120 of the piston unites 110 (compare FIG. 1). i.e., there are a plurality of eighteen rows of five air chambers 320 arranged side by side so that the air chambers 320 are arranged in an array of 5×18 alike the array of 5×18 pistons 120. Each of the eighteen rows of air chambers 320 are surrounded by the elevated edges 332. The eighteen elevated edges 332 surrounding a row of five air chambers allow for forming an airtight sealing between the air pressure distribution plate 103 and the membrane 220 (compare FIG. 2). The five air chambers 320 of each row are connected by air ducts 430 between two neighbouring air chambers 320. The air ducts 430 provide an air pressure exchange between the air chambers 320 for each of the eighteen rows. The air chamber 320, the air ducts 430 and the elevated edges 332 may be integrated parts of the air pressure distribution plate 103 and may be made from one piece. However, to make the construction clearer the detail of a row of air chambers 320, of the air ducts 430, and of the elevated edge 332 is shown in an enlarged version separately in FIG. 3.

Two air distribution manifolds 131 are fixed to the air pressure distribution plate 103 and are each feed by air pressure terminals 130. A cross-section "A" indicated by a dashed line through the detail of the test system 100, i.e. comprising also the piston unit support plate 102, will make clear the working mechanism of the test system 100.

Figure 4A:
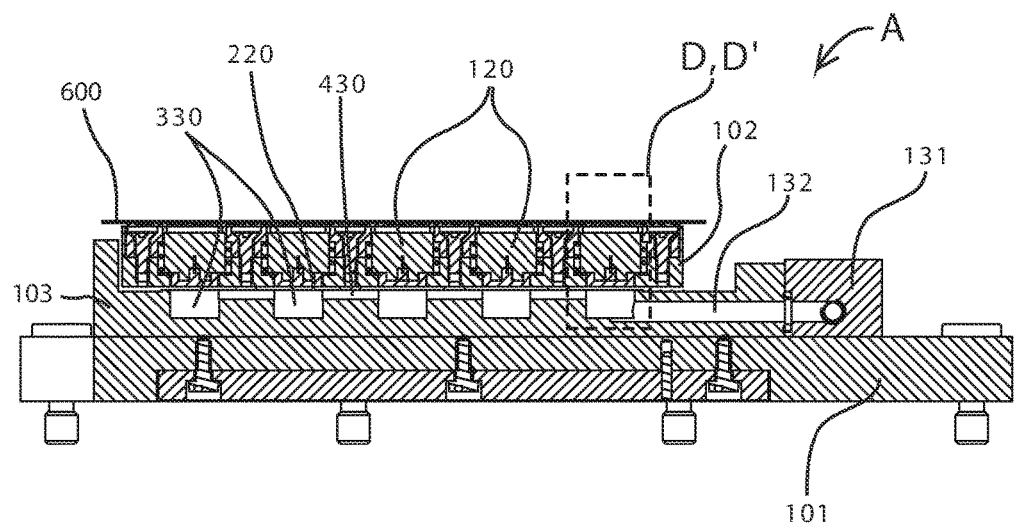
FIG. 4a shows a cross-sectional view through a piston unit of the test system

FIG. 4a shows the cross-sectional view "A" through the test system 100 wherein one piston unit 110 comprises a row of five pistons 120. The air pressure manifold 131 distributes a specific air pressure to the air bore hole 132. The air bore hole 132 pipes the air pressure to the first of the five air chambers 320. The five air chambers 320 are connected by the air ducts 430 by allowing an air pressure exchange between the five air chambers 320. One respective piston 120 is mounted above each of the five air chambers 320. The membrane 220 is located between the five air chambers 320 and the five respective pistons 120. A carrier 600 extends above the five pistons 120. The air bore hole 132, the five air chambers 320, and the four respective air ducts 430 may be integral parts of the air pressure distribution plate 103 which is mounted on the base plate 101. The pistons 120 are mounted by the piston unit 110 on the piston unit support plate 102.

Figure 4B:
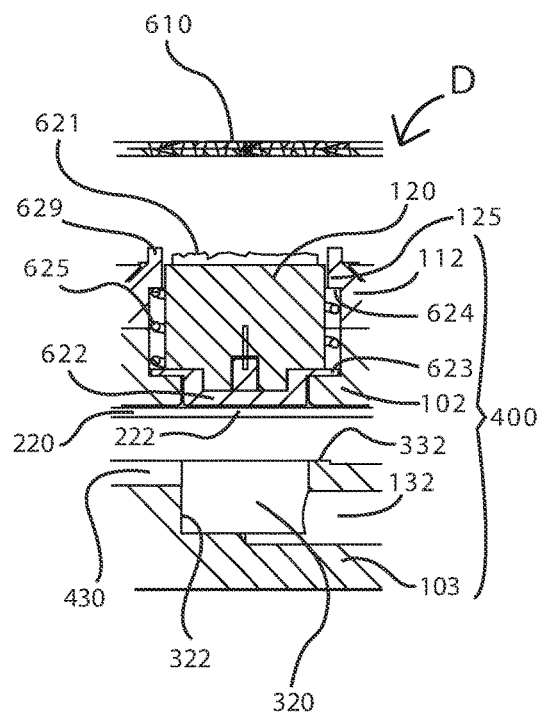
FIG. 4b shows a detail of a cross-sectional view of a test device with a piston in rest position

FIG. 4b shows a detail "D" of a test device 400 in a cross-sectional view in a partially exploded view, wherein the piston 120 is in a rest position. The air bore hole 132, the air chamber 320, and the air duct 430 are integral parts of or being milled in the air pressure distribution plate 103. The air pressure distribution plate 103 comprises the elevated edge 332 surrounding the air chambers 320. The membrane 220 being detached in this view from the air pressure distribution plate 103 is regularly pressed towards the elevated edge 332 so that the five air chambers 320 form a mutual reservoir for the air pressure being equally distributed by the air ducts 430. The membrane 220 is located between the air chamber 320 and the piston 120. The piston 120 comprises a piston base 622 which terminates evenly or on the same level like the piston unit support plate 102. Since the piston unit support plate 102 is mounted on the air pressure distribution plate 102 the membrane 220 is airtightly pressed between the piston 120 and the air chamber 320. An increased air pressure in the air chamber 320 would cause an elevation of the piston 120 which is described with FIG. 4c. If there is no increased air pressure in the air chamber 320 the piston 120 is forced into the rest position. To reach this, the piston base 622 has a cup form wherein a flange like edge 623 of the piston base 622 allows for supporting the piston 120 against a support flange 626 of the piston unit support plate 102. A return spring 625 urges the piston 120 in rest position since the return spring 625 is mounted between a support flange 624 of the piston support 112 and the flange like edge 623 of the piston base 622. Thus, the biased return spring 625 forces the free movable piston 120 towards the air chamber 320.

Figure 4C:
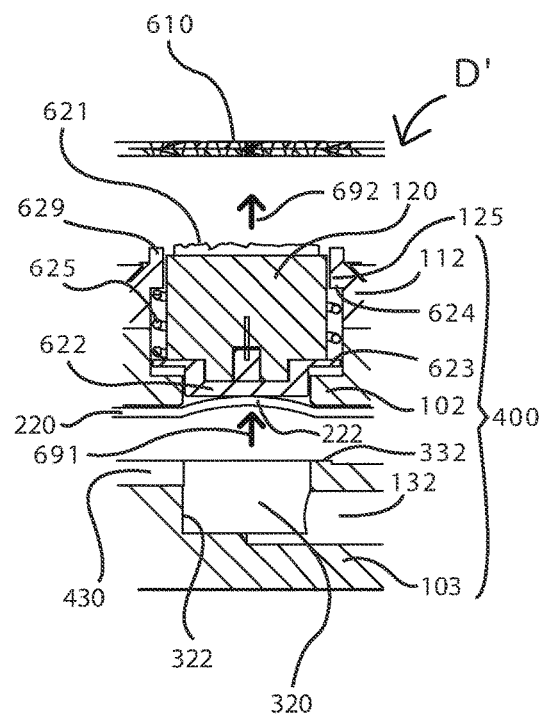
FIG. 4c shows a detail of a cross-sectional view of the test device with a piston in an elevated position

FIG. 4c shows detail "DT" of the test device 400 when the piston 120 is in an elevated position. The air pressure is increased so that the force of the return spring 625 may be overcome. Since the elevated edge 332 forms an airtight seal between the air chamber 320 and the membrane 220, the membrane 220 bulges in the direction 691 towards the piston 120 which in turn is lifted in the same direction 692 towards the carrier 600. Thus, the piston 120 reaches the elevated position. The piston 120 comprises a fingerprint dummy 621 on top towards the carrier 600 so that the fingerprint dummy 621 can simulate a pressed fingerprint when the piston 120 is urged out of the rest position towards the elevated position.

FIG. 5 shows a cross-sectional view "B" (compare FIG. 3) through a vacuum supply of the test system 100. The vacuum fitting 150 supplies a vacuum for the vacuum cups 250 via a vacuum duct 550 extending through the base plate 101. The vacuum supply extends through the air pressure distribution plate 103 and through the piston unit support plate 102. The vacuum cups 250 protrude from the piston unit support plate 102. The carrier 600 can be sucked towards the piston unit support plate 102 by the resilient vacuum cups 250. The carrier 600 has an array of 5×18 fingerprint sensors 610 interacting with the array of 5×18 fingerprint dummies 621 when the 5×18 pistons 120 are forced into the elevated position by mutually increasing the air pressure in the air chambers 320.

Figure 6:
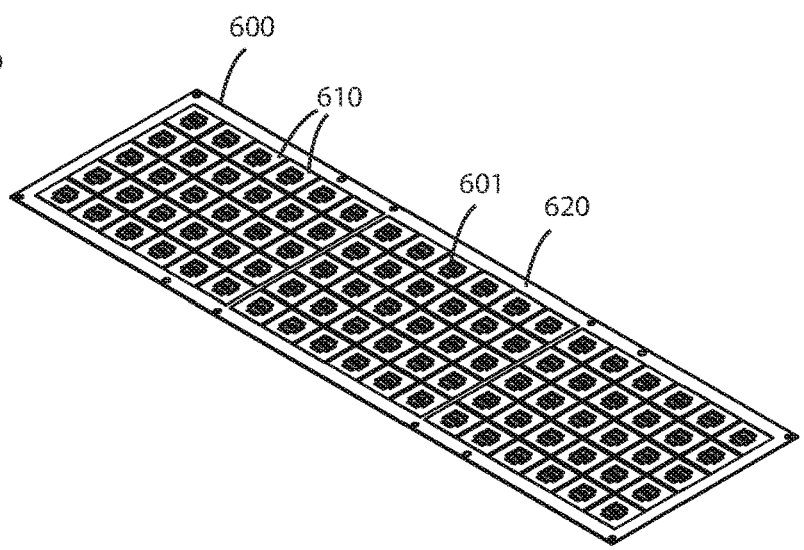
FIG. 6 shows a carrier in a top view

As an example, for a carrier 600, FIG. 6 is showing a typical strip comprising in a top view. The strip or carrier 600 comprises a carrier plate 620 on which a plurality of electronic components 610 are arranged in an array. On the top view side of the carrier 600 the electronic components 610 (such as fingerprint sensors) may have the terminals 601 of the electronic components 610 for contacting to the contacts of a contact socket (not shown).

Figure 7:
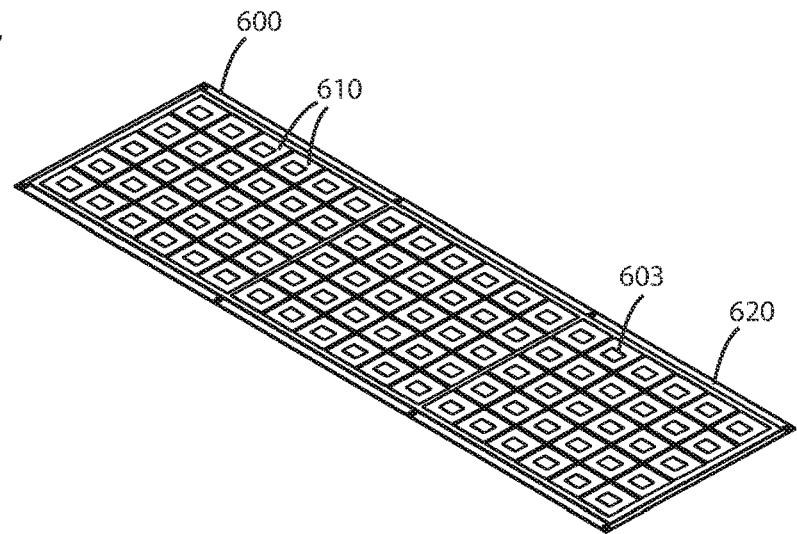
FIG. 7 shows a carrier in a bottom view

FIG. 7 shows the carrier 600 or strip in a bottom view. On the bottom view the electronic components 610 may have the fingerprint sensor area 603 on which the fingerprint dummy 621 may be pressed.

Figure 8:
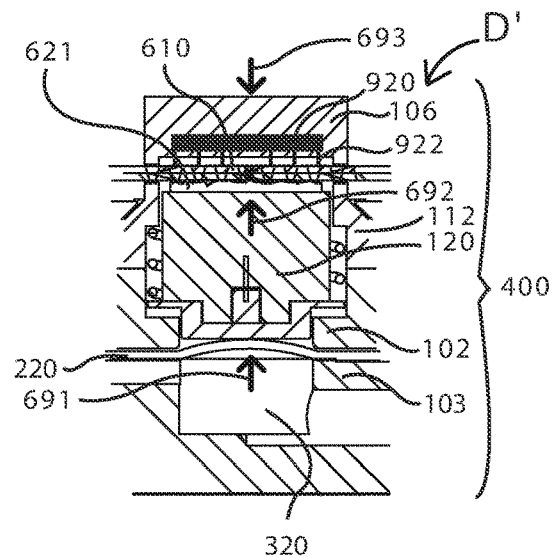
FIG. 8 shows a detail of a cross-sectional view of a test device including a contact block

FIG. 8 shows a detail D' of a cross-sectional view of a test device 400 including a contact block 106. As already described with FIG. 4c the increased air pressure in the air chamber 320 causes the membrane 220 to bulge in the direction 691 which in turn causes the piston 120 to lift off its rest position the same direction 692 and to be pressed against the mechanical pressure sensor 610 to be tested. A contact block 106 may exert a counterforce 693 on the mechanical pressure sensor 610 (or fingerprint dummy) against the mechanical pressure dummy 621 (or fingerprint dummy) which mechanical pressure sensor 610 would otherwise be caused to be lifted off as well by the pressure exerted by the piston 120. In detail, also contacts 922 of a socket 920 being a part of the contact block 106 may contact to contact terminals (not shown) of the mechanical pressure sensor 610.

Figure 9:
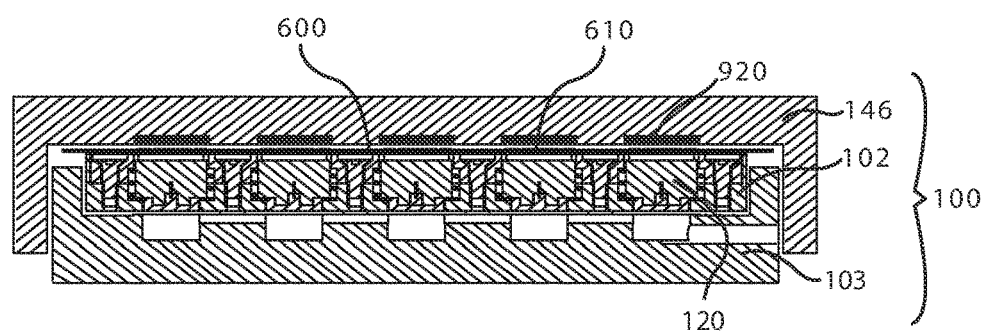
FIG. 9 shows a cross-sectional view through a test system including a contact block support

FIG. 9 shows a cross-sectional view through a test system 100 including a contact block support 146 comprising five sockets 920. The sockets 920 may be aligned with the mechanical pressure sensors 610 of the carrier 600 so that the mechanical pressure sensors 610 can be tested.

Figure 10:
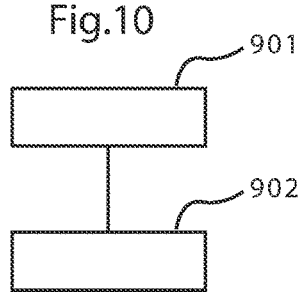
FIG. 10 shows a schematic view of the method

FIG. 10 shows a schematic view of the method comprising increasing 901 the air pressure in the air chamber 320 so that the mechanical pressure dummy 621 is pressed 902 in a test position.

It should be noted that the term "comprising" does not exclude other elements or features and the "a" or "an" does not exclude a plurality. Also elements described in association with different embodiments may be combined. It should also be noted that reference signs in the claims shall not be construed as limiting the scope of the claims.

The invention claimed is:

1. A test device for testing a mechanical pressure sensor, the test device comprises:
   a mechanical pressure dummy,
   a piston, and
   an air chamber having an elastic side section,
   wherein the air chamber is configured such that an increasing air pressure in the air chamber causes the elastic side section to bulge and to press the mechanical pressure dummy in a test position, and
   wherein the mechanical pressure dummy is arranged at one piston end of the piston, and wherein the elastic side section is arranged at an opposite piston end of the piston.

2. The test device according to claim 1, wherein the bulging of the elastic side section goes in the same direction like a movement of the mechanical pressure dummy.

3. The test device according to claim 1, wherein the air chamber comprises an elevated edge so that pressing the elastic side section against the elevated edge makes an air-tight seal.

4. The test device according to claim 1, wherein the piston is guidable by a piston guide so that the mechanical pressure dummy is moveable perpendicularly into the test position.

5. The test device according to claim 4, further comprising a return spring clamped between the piston and the piston guide so that the piston is held in an initial position when there is ambient air pressure in the air chamber.

6. A test system for parallel testing a plurality of mechanical pressure sensors, the test system comprises:
a plurality of test devices according to claim 1,
wherein the air chambers are coupled by air ducts so that there is a pressure balance between the air chambers.

7. A test system for parallel testing of a plurality of mechanical pressure sensors, the test system comprises:
a plurality of mechanical pressure dummies,
a plurality of pistons, and
a plurality of air chambers having each an elastic side section,
wherein the plurality of elastic side sections are arranged so that increasing an air pressure in the plurality of air chambers causes each of the elastic side sections to bulge and to press each of the plurality of mechanical pressure dummies in a test position,
wherein the mechanical pressure dummies are arranged at one piston end of a respective piston, and
wherein the elastic side sections are arranged at an opposite piston end of a respective piston.

8. The test system according to claim 7, wherein the bulging of the elastic side sections goes in the same direction like the movement of the mechanical pressure dummies.

9. The test system according to claim 7, wherein the air chambers comprise elevated edges so that pressing the elastic side sections against the elevated edges makes air-tight seals.

10. The test system according to claim 7, further comprising a plurality of air ducts, wherein the air chambers are coupled by the air ducts so that there is a pressure balance between the air chambers.

11. The test system according to claim 7, wherein the pistons are guideable by piston guides so that the mechanical pressure dummies are moveable mutually and perpendicularly towards the mechanical pressure sensors.

12. The test system according to claim 11, further comprising a plurality of return springs clamped between the pistons and the piston guides so that the pistons are held in initial positions when there is ambient air pressure in the air chambers.

13. A method of testing a mechanical pressure sensor, the method comprises:
providing a mechanical pressure dummy,
providing an air chamber having an elastic side section,
increasing an air pressure in the air chamber so that the elastic side section bulges and causes the mechanical pressure dummy to be pressed in a test position,
arranging the mechanical pressure dummy at one piston end of a piston, and
arranging the elastic side section at an opposite piston end of the piston.

14. The method according to claim 13, wherein the bulging of the elastic side section goes in the same direction like a movement of the mechanical pressure dummy.

15. The method according to claim 13, further comprising pressing the elastic side sections against elevated edges of the air chambers to make air-tight seals.

16. The method according to claim 13, wherein the piston is guided by a piston guide so that the mechanical pressure dummy is moved perpendicularly in the test position.

17. The method according to claim 13, further comprising coupling a plurality of air chambers by air ducts so that there is a pressure balance between the air chambers.

* * * * *